US 8,585,698 B2

(12) United States Patent
Suzuki

(10) Patent No.: US 8,585,698 B2
(45) Date of Patent: Nov. 19, 2013

(54) TREATMENT DEVICE FOR ENDOSCOPE

(75) Inventor: Keita Suzuki, Tokyo (JP)

(73) Assignee: Olympus Medical Systems Corp., Tokyo (JP)

(*) Notice: Subject to any disclaimer, the term of this patent is extended or adjusted under 35 U.S.C. 154(b) by 330 days.

(21) Appl. No.: 13/165,105

(22) Filed: Jun. 21, 2011

(65) Prior Publication Data

US 2011/0319709 A1    Dec. 29, 2011

Related U.S. Application Data

(63) Continuation of application No. PCT/JP2010/070196, filed on Nov. 12, 2010.

(30) Foreign Application Priority Data

Dec. 22, 2009    (JP) ............................... P2009-291200

(51) Int. Cl.
*A61B 18/14*    (2006.01)

(52) U.S. Cl.
USPC ............... 606/46; 606/41; 600/104; 600/105; 600/106

(58) Field of Classification Search
USPC .................. 606/41, 46; 600/104–106
See application file for complete search history.

(56) References Cited

U.S. PATENT DOCUMENTS

| | | | | |
|---|---|---|---|---|
| 4,708,137 | A * | 11/1987 | Tsukagoshi | 606/46 |
| 8,048,073 | B2 * | 11/2011 | Nakamura et al. | 606/46 |
| 8,187,271 | B2 * | 5/2012 | Yahagi et al. | 606/46 |
| 2004/0172018 | A1 * | 9/2004 | Okada | 606/46 |
| 2004/0210284 | A1 * | 10/2004 | Okada | 607/96 |
| 2006/0276784 | A1 * | 12/2006 | Miyajima et al. | 606/46 |
| 2007/0088354 | A1 * | 4/2007 | Sugita | 606/46 |

FOREIGN PATENT DOCUMENTS

| | | |
|---|---|---|
| EP | 1 985 250 A2 | 10/2008 |
| JP | UM-A-61-191012 | 11/1986 |
| JP | 4-329944 A | 11/1992 |
| JP | A-2004-000544 | 1/2004 |
| JP | A-2008-272204 | 11/2008 |
| JP | A-2008-272365 | 11/2008 |

OTHER PUBLICATIONS

European Supplementary Search Report dated Oct. 25, 2011 from corresponding European Application No. 10 83 9086.5.

* cited by examiner

*Primary Examiner* — Michael Peffley
*Assistant Examiner* — Khadijeh Vahdat
(74) *Attorney, Agent, or Firm* — Scully, Scott, Murphy & Presser, P.C.

(57) ABSTRACT

A treatment device for an endoscope includes an operating wire having a treatment section at a distal end thereof, a first sheath through which the operating wire is inserted, a second sheath into which the first sheath is inserted, a locking portion provided in the treatment section to advance or retreat, a first stopper that regulates advance movement of the locking portion, a second stopper that regulates retreat movement of the locking portion, and a sheath operating portion that advances or retreats the second sheath between a first positional relationship and a second positional relationship. The first stopper is provided in the first sheath via a connecting portion that extends toward the front side from a distal end of the first sheath, and the second stopper is provided in the second sheath on the rear side of the first stopper in the direction of the axis.

8 Claims, 13 Drawing Sheets

TREATMENT DEVICE FOR ENDOSCOPE

This application is a continuation application based on PCT International Application No. PCT/JP2010/070196, filed on Nov. 12, 2010, claiming priority on the basis of Japanese Patent Application No. 2009-291200, filed on Dec. 22, 2009. The contents of both the PCT International Application and the Japanese Patent Application are incorporated herein by reference.

BACKGROUND OF THE INVENTION

1. Field of the invention

The present invention relates to a treatment device for an endoscope used after being inserted into a channel for operation of an endoscope apparatus.

2. Description of Related Art

In the related art, a treatment device for an endoscope including a needle knife (treatment section), which is endoscopically inserted into a body cavity, and applies a high-frequency current to the needle knife so as to excise a membrane or the like, is known (for example, refer to JP-UM-A-61-191012).

Such a treatment device for an endoscope is configured such that a treatment section, such as the needle knife that performs a treatment on an affected part, is attached to a distal end of an operating wire inserted through an insulating sheath inserted into a channel of an endoscope. This treatment section is allowed to protrude or retract from the distal end of the sheath by operating the operating section to which a proximal end of the operating wire is fixed.

In the treatment device for an endoscope, the protruding length of the treatment section from the distal end of the sheath is generally short, and adjustment of the protruding length is not easy. Additionally, since the endoscope is inserted into a body cavity while being intricately bent, in a treatment device for an endoscope inserted into the endoscope, the operating amount of the operating section and the protruding or retracting amount of a distal end member do not correspond to 1 to 1 in many cases. For this reason, in the present situation, it is possible to precisely adjust the protruding length of the treatment section only in two states: when the treatment section is fully protruded from the sheath and when the treatment section is accommodated within the sheath.

In order to improve this problem, an incision device for an endoscope that provides a locking portion with a larger diameter than the internal diameter of a sheath in an electrode or operating section located within the sheath, thereby applying resistance to the advancing or retreating of the treatment section and allowing for fine adjustment of the protruding length is proposed (for example, refer to JP-A-No. 2004-544).

SUMMARY OF THE INVENTION

According to a first aspect of the present invention, a treatment device for an endoscope includes an operating wire having a treatment section that performs a treatment on a tissue in a body cavity at a distal end thereof and being capable of being advanced and retreated in the direction of an axis; a first sheath through which the operating wire is inserted; a second sheath into which the first sheath is inserted and from a distal end of which the treatment section protrudes; a locking portion provided in the operating wire or the treatment section to advance or retreat in the direction of the axis with advance or retreat operation of the operating wire; a first stopper that regulates advance movement of the locking portion; a second stopper that regulates retreat movement of the locking portion; and a sheath operating portion that advances or retreats the second sheath between a first positional relationship and a second positional relationship such that the second sheath has a different position relative to the first sheath in the direction of the axis. Here, the first stopper is provided in the first sheath via a connecting portion that extends toward the front side from a distal end of the first sheath, and the second stopper is provided in the second sheath on the rear side of the first stopper in the direction of the axis.

According to a second aspect of the present invention, the distance between the first stopper and the second stopper in the direction of the axis may vary in a case where the second sheath is located in the first positional relationship and a case where the second sheath is located in the second positional relationship.

According to a third aspect of the present invention, the treatment device for an endoscope may further include a third stopper provided at a distal end of the first sheath to abut the second stopper in the first positional relationship to restrict retreat movement of the second sheath with respect to the first sheath.

According to a fourth aspect of the present invention, the treatment device for an endoscope may further include a third stopper provided at a distal end of the first sheath to abut the second stopper in the first positional relationship to restrict retreat movement of the second sheath with respect to the first sheath.

According to a fifth aspect of the present invention, the treatment device for an endoscope may further include a fourth stopper provided at the connecting portion to abut the second stopper in the second positional relationship to restrict advance movement of the second sheath with respect to the first sheath.

According to a sixth aspect of the present invention, the sheath operating portion may include a rotation handle section allowed to be rotationally operated around the direction of the axis, and the second sheath may move in the direction of the axis relative to the first sheath by rotationally operating the rotation handle section.

According to a seventh aspect of the present invention, the treatment device for an endoscope may further include a cam groove formed in an inner peripheral surface of the rotation handle section that has a cylindrical shape and twisted around the axis, and a movable member made movable in the direction of the axis and connected to the second sheath. A portion of the movable member may be inserted into the cam groove.

According to an eighth aspect of the present invention, the treatment device for an endoscope may further include a pair of elastic members respectively provided on both sides of the movable member in the direction of the axis to connect the movable member and the second sheath.

DETAILED DESCRIPTION OF THE INVENTION

Hereinafter, an embodiment of the present invention will be described specifically with reference to FIGS. 1 to 13D.

Figure 1:
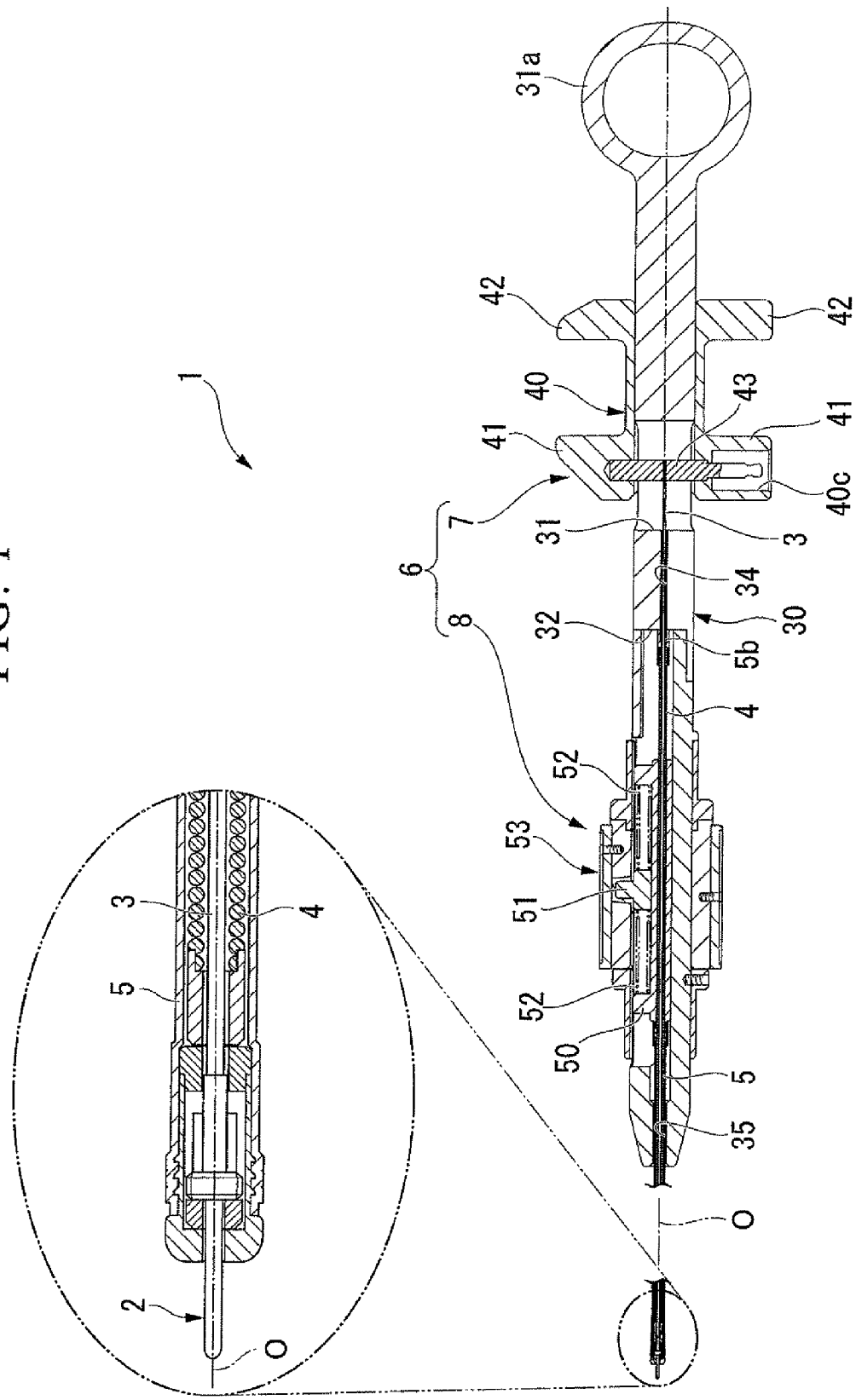
FIG. 1 is a cross-sectional view of an overall treatment device for an endoscope related to an embodiment.
Figure 2:
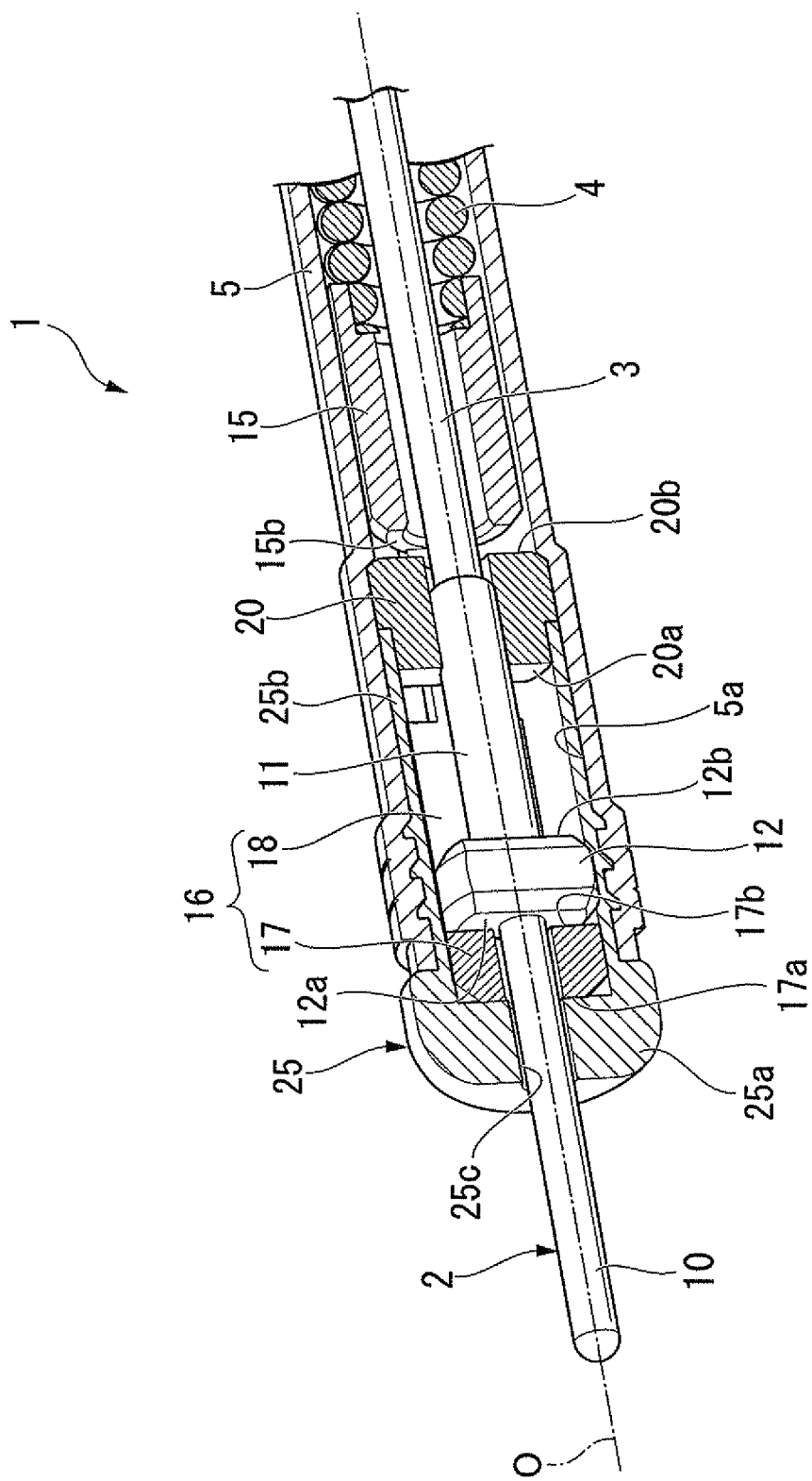
FIG. 2 is a perspective cross-sectional view of a distal end side of the treatment device for an endoscope related to the embodiment.
Figure 3:
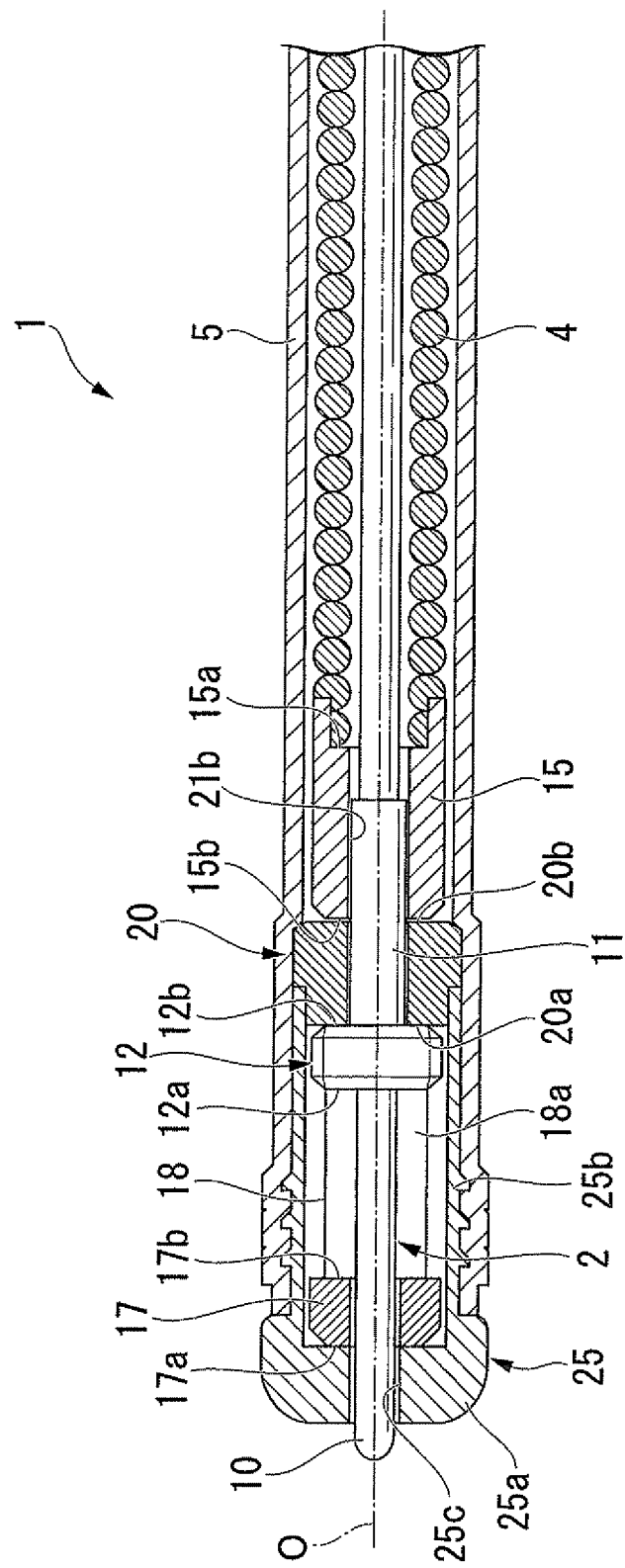
FIG. 3 is a longitudinal cross-sectional view of the distal end side of the treatment device for an endoscope related to the embodiment.
Figure 4:
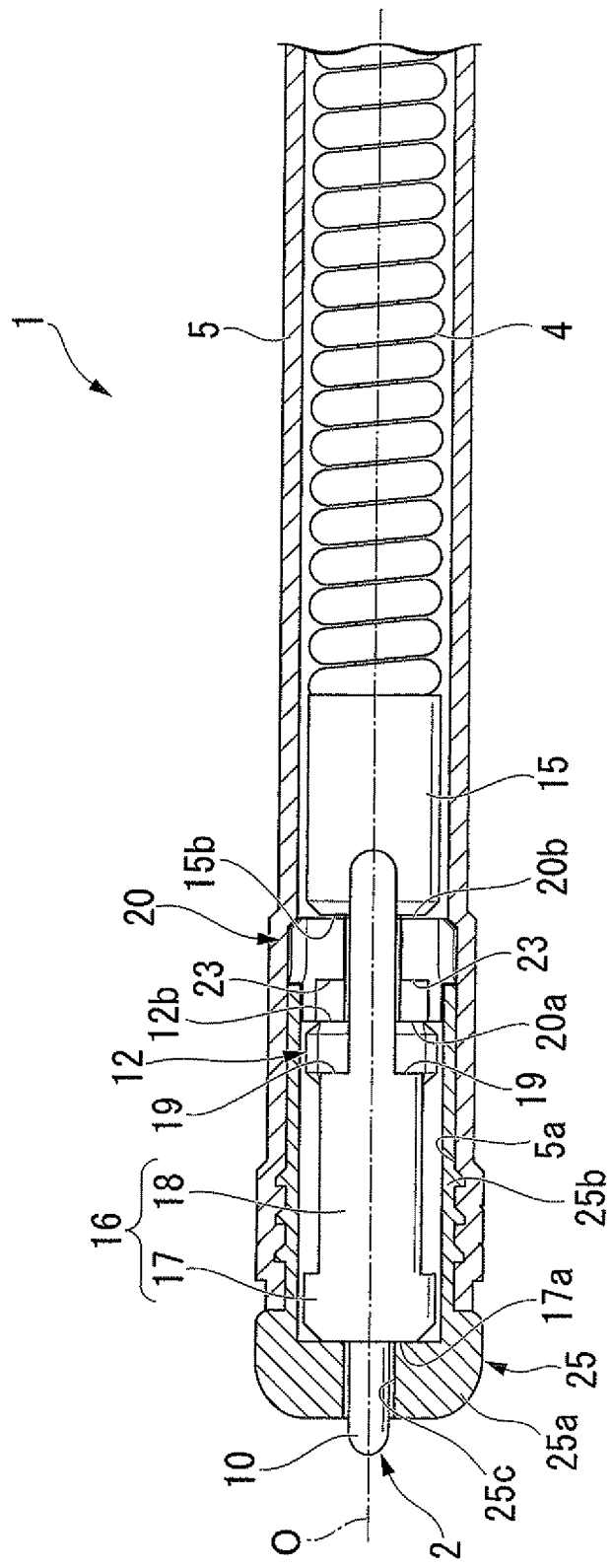
FIG. 4 is a side view of a distal end side of the treatment device for an endoscope related to the embodiment.

As shown in FIG. 1, a treatment device 1 for an endoscope (hereinafter simply referred to as a "treatment device") of the present embodiment includes a treatment section 2 for performing a treatment on a tissue in a body cavity, an operating wire 3 connected to a proximal end of the treatment section 2, a first sheath 4 through which the operating wire 3 is inserted, a second sheath 5 into which the first sheath 4 is inserted, and from the distal end of which the treatment section 2 is allowed to protrude or retract, and an operating section 6 that adjusts the protruding length of the treatment section 2. The operating section 6 includes a wire operating portion 7 that operates the operating wire 3, and a sheath operating portion 8 capable of being supported by moving the first sheath 4 and the second sheath 5 relative to each other.

The treatment section 2, as shown in FIGS. 2 to 5, includes a metal needle-like scalpel 10 that extends with an axis O as a center on the distal end side. As a high-frequency power source is electrically connected to the needle-like scalpel 10, incision treatment or the like of a tissue in a body cavity can be performed. In the present embodiment, the needle-like scalpel 10 is formed in the shape of, for example, a needle with a length of about 3 mm. Instead of this, however, the scalpel may have a spatula shape or a hook shape.

A wire coupling portion 11 that has slightly larger diameter than the needle-like scalpel 10 and extends with the axis O, as a center is provided on a rear end side of the treatment section 2. As the wire coupling portion 11 is coupled to the distal end of the operating wire 3, the treatment section 2 is integrally fixed to the operating wire 3.

A locking portion 12 is integrally provided between the needle-like scalpel 10 and the wire coupling portion 11.

Figure 5:
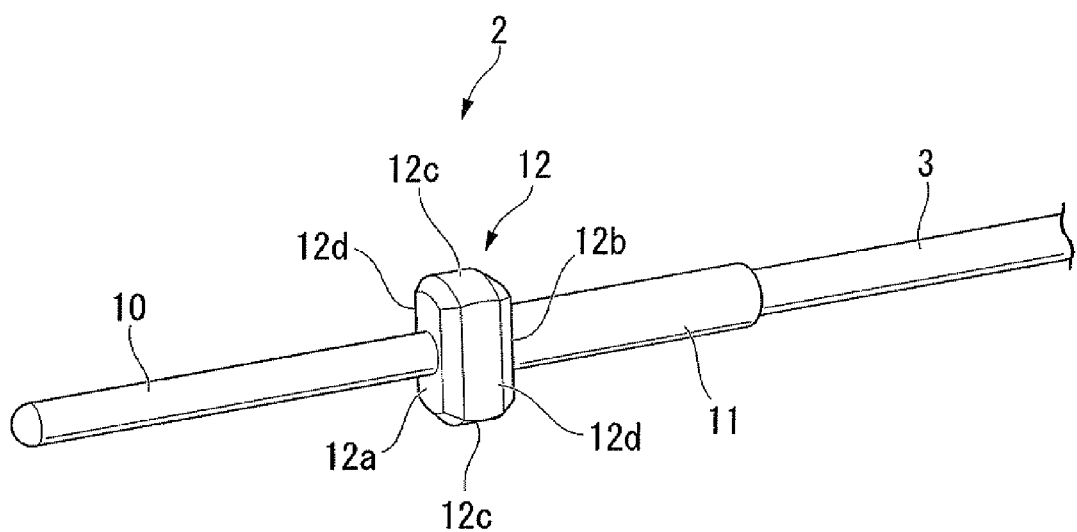
FIG. 5 is a perspective view of a treatment section.

The locking portion 12 has a flange shape that overhangs to both sides in one direction orthogonal to the axis O. Specifically, as shown in FIG. 5, the locking portion includes a locking portion distal end face 12a that is directed to the distal end side, and a locking portion rear end face 12b that is directed to the rear end side. The locking portion distal end face 12a and the locking portion rear end face 12b have a flat shape orthogonal to the axis O, respectively. Both end faces of the locking portion 12 in one direction orthogonal to the axis O are circular-arc faces 12c and 12c having the axis O as a center. A pair of faces connected to the circular-arc faces 12c and 12c, the locking portion distal end face 12a, and the locking portion rear end face 12b, respectively, and parallel to the axis O is formed as lateral faces 12d and 12d.

The locking portion distal end face 12a is allowed to face a first stopper distal end face 17a of a first stopper 17 that will be described below. The locking portion rear end face 12b is capable of abutting a second stopper distal end face 20a of a second stopper 20 that will be described below.

The operating wire 3, as shown in FIGS. 1 to 4, is a bendable wire that extends along the axis O and is made of, for example, a metal, such as stainless steel, and is inserted through the first sheath 4. The distal end of the operating wire 3 is coupled to the wire coupling portion 11 of the treatment section 2, and the rear end thereof is coupled to the wire operating portion 7 in the operating section 6.

The first sheath 4, as shown in FIGS. 1 to 4 and 6A to 6B, has a coil shape that is formed by densely winding a metal wire in the shape of a loop with the axis O as a center, and the operating wire 3 is inserted through the inner peripheral side of the coil shape of the first sheath 4. A rear end of the first sheath 4 is coupled to the operating section 6, and a third stopper 15 and a guide stopper 16 are provided on the distal end side of the first sheath.

Figure 6A:
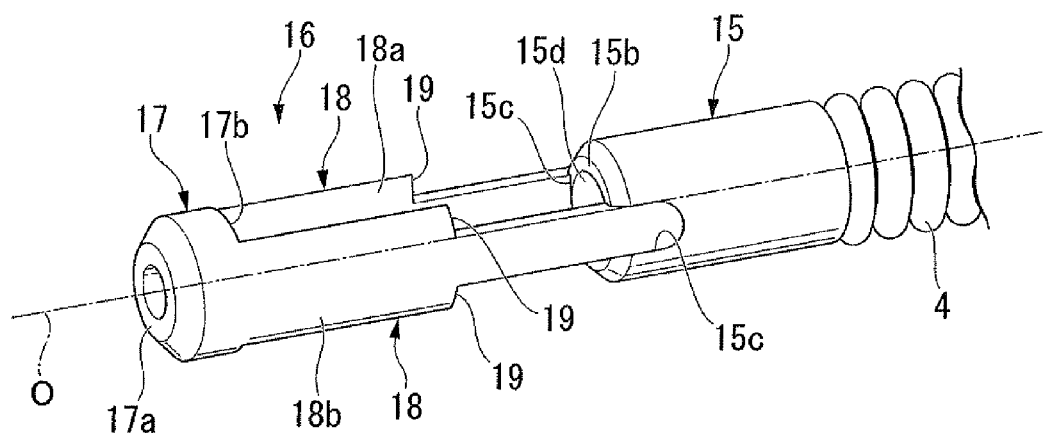
FIG. 6A is a perspective view of a first sheath, a third stopper, and a guide stopper 16.
Figure 6B:
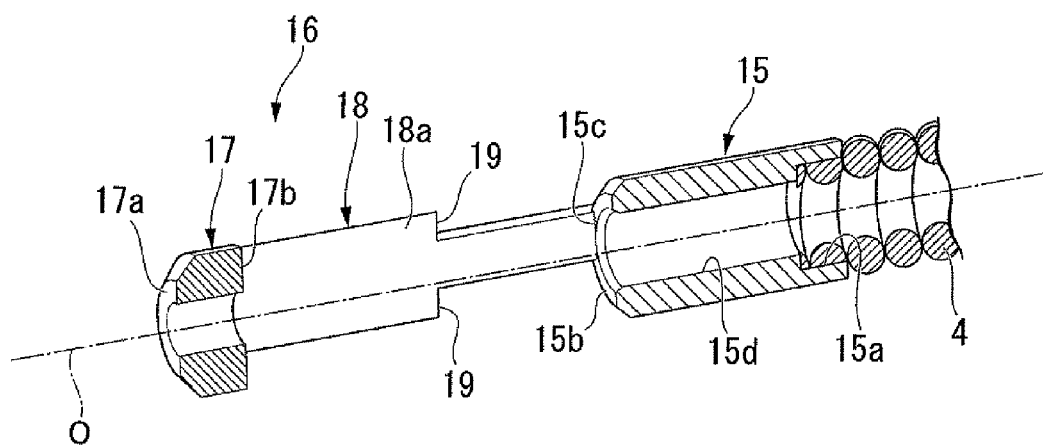
FIG. 6B is a cross-sectional perspective view of the first sheath, the third stopper, and the guide stopper 16.

Specifically, as shown in FIGS. 6A and 6B, the third stopper 15 has a cylindrical shape having the axis O as a center, an outer peripheral surface thereof has a slightly greater external diameter than the external diameter of the first sheath 4, and an inner peripheral surface 15d thereof has an internal diameter such that the operating wire 3 and the wire coupling portion 11 can be inserted therethrough. A rear end opening in an inner peripheral surface of the third stopper 15 is formed as a sheath coupling portion 15a whose internal diameter is enlarged one step, and the third stopper 15 is coupled to the first sheath 4 as a sheath coupling portion 15a fits to a distal end of the first sheath 4 from the outside.

The end face of the third stopper 15 that is directed to the distal end side is formed as a third stopper distal end face 15b that has an annular shape and has a flat face orthogonal to the axis O. The third stopper distal end face 15b is capable of abutting a second stopper rear end face 20b of the second stopper 20 that will be described below.

Moreover, connecting portion coupling grooves 15c and 15c to which connecting portions 18 and 18 of the guide stopper 16 that will be described below can be coupled are formed at an interval of 180° in a circumferential direction at a distal end portion of an outer peripheral surface of the third stopper 15.

Specifically, as shown in FIGS. 6A and 6B, the guide stopper 16 is attached to a distal end side of the third stopper 15. The guide stopper 16 includes a first stopper 17 that has almost the same diameter as the circular-arc face 12c of the locking portion 12 and has the axis O as a center, and the pair of connecting portions 18 and 18 that couples the first stopper 17 to the third stopper 15. Due to the presence of the connecting portions 18 and 18, the first stopper 17 is provided so as to separate to the front side in the direction of the axis O of the third stopper 15.

The face of the first stopper 17 that is directed to the distal end side is formed as a first stopper distal end face 17a that has an annular shape having the axis O as a center and has a flat shape orthogonal to the axis O. The face of the first stopper 17 that is directed to the rear end side is formed as a first stopper rear end face 17b that has an annular shape having the axis O as a center and has a flat shape orthogonal to the axis O, similarly to the first stopper distal end face 17a. In addition, the first stopper distal end face 17a is capable of abutting a distal end lid portion 25a of a distal end member 25 that will be described below.

The pair of connecting portions 18 extends toward the rear end side from positions where the connecting portions oppose each other at 180° across the axis O in the first stopper rear end face 17b of the first stopper 17. The faces of the connecting portions 18 that oppose each other are formed as connecting portion opposed faces 18a that are parallel to the axis O and parallel to each other. The distance between the connecting portion opposed faces 18a is a length that is almost the same as or slightly greater than the distance of the lateral faces 12d of the locking portion 12.

The outer peripheral surfaces of the pair of connecting portions 18, that is, the opposite faces of the connecting portion opposed faces 18a in the connecting portions 18 are formed as connecting portion outer peripheral surfaces 18b that have a cylindrical surface shape with almost the same diameter as the circular-arc face 12c of the locking portion 12, respectively. That is, the opposite faces of the connecting portion opposed faces 18a are formed as curved surfaces that are flush with the outer peripheral surface of the first stopper 17.

The connecting portion 18 is formed such that the circumferential width thereof having the axis O as a center is one-step narrower at a rear-side portion than at a front-side portion. A stepped portion between the front-side portion and the rear-side portion is formed as a fourth stopper 19 that has a flat shape orthogonal to the axis O, and is directed to the rear end side. A pair of the fourth stoppers 19 is provided so as to be separated by a predetermined interval (the circumferential length of the rear-side portion of the connecting portion 18) in the circumferential direction in each of the connecting portions 18 and 18. That is, a total of four fourth stoppers 19 are provided at the same position in the direction of the axis O. In addition, the fourth stoppers 19 are capable of abutting a fourth stopper abutting face 23 in the second stopper 20.

Figure 7:
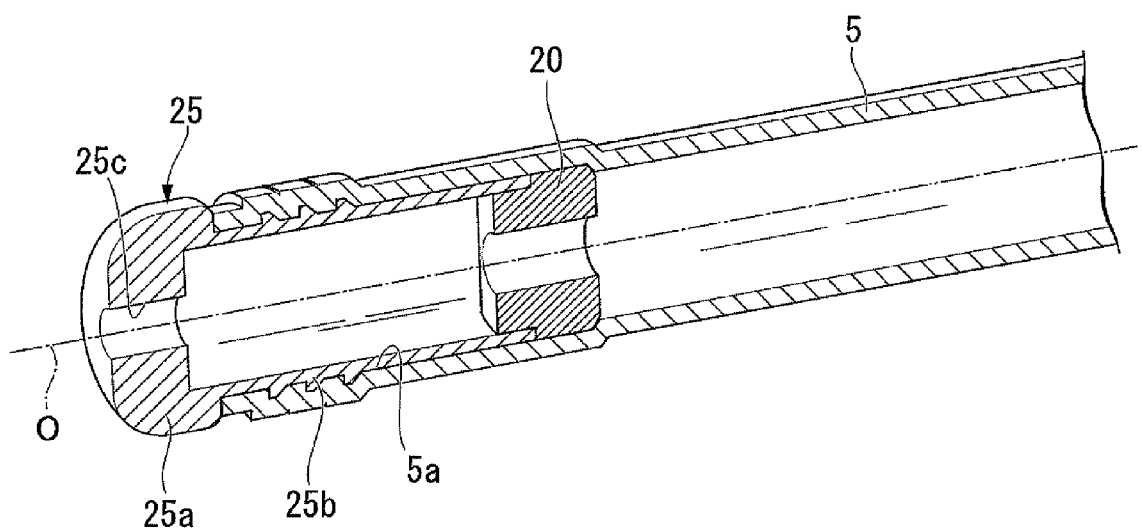
FIG. 7 is a perspective view of a second sheath, a second stopper, and a distal end member.

As shown in FIGS. 1 to 4 and 7, the second sheath 5 has a tube shape formed of an insulating material, and covers the external surface of the first sheath 4 to secure insulation. A rear end of this second sheath 5 is connected to the sheath operating portion 8 that will be described below. Specifically, as shown in FIG. 7, a portion on the distal end side of the second sheath 5 is formed as a portion 5a to be inserted that is formed such that inner periphery and outer periphery are made one step larger than the other portions. The second stopper 20 is provided at a stepped portion between the portion 5a to be inserted and the other portions in the inner peripheral surface of the second sheath 5, and a distal end member 25 is provided at a front end (front end of the second sheath 5) of the portion 5a to be inserted.

Figure 8A:
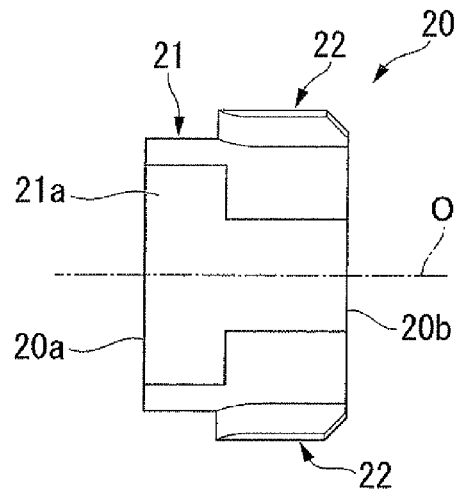
FIG. 8A is a side view of the second stopper.
Figure 8B:
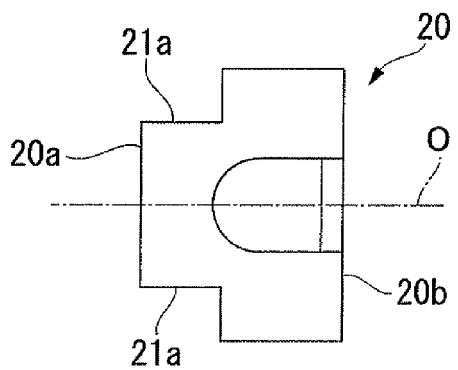
FIG. 8B is a plan view of the second stopper.
Figure 8C:
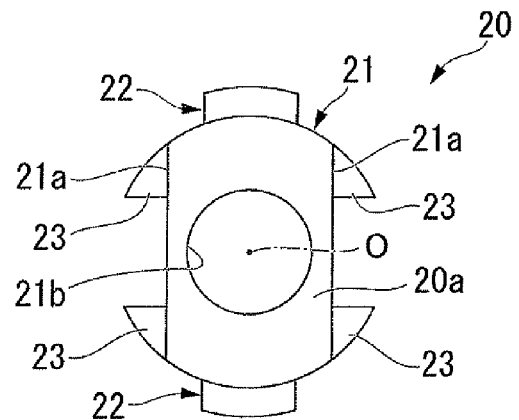
FIG. 8C is a front view when the second stopper is seen from the distal end side.

Specifically, as shown in FIGS. 8A to 8C, the second stopper 20 is composed of a second stopper body 21 that has a substantially tubular shape having the axis O as a center, and a pair of projection portions 22 and 22 formed so as to protrude from the outer peripheral surface of this second stopper body 21.

The internal diameter of an inner peripheral surface 21b of the second stopper body 21 is set to a diameter such that the wire coupling portion 11 of the treatment section 2 can be inserted therethrough, and the external diameter thereof is set to be slightly smaller than the internal diameter of the portion 5a to be inserted of the second sheath 5. Additionally, a pair of T-shaped flat faces 21a and 21a that is formed so as to be cut out in the shape of the letter T laterally in a side view shown in FIG. 8A is formed at places that opposes each other at 180° in the circumferential direction in the outer peripheral surface of the second stopper 20. The spacing between the T-shaped flat faces 21a and 21a is set to a spacing that is almost equal to or slightly smaller than the spacing between the connecting portion opposed faces 18a of the connecting portions 18 and 18. The circumferential width in a front-side portion of the T-shaped flat face 21a or 21a is set to be almost equal to that of the front-side portion of the connecting portion 18, and the circumferential width in a rear-side portion of the T-shaped flat face 21a or 21a is set to be almost equal to that of the rear-side portion of the connecting portion 18.

Moreover, four faces that are exposed to the front side in the direction of the axis O as the second stopper body 21 is cut out in the shape of the letter T laterally in a side view as described above are formed as fourth stopper abutting faces 23 that have a substantially fan-shaped shape and have a flat shape orthogonal to the axis O, in a front view shown in FIG. 8C. The fourth stopper abutting faces 23 abuts the fourth stoppers 19, respectively.

Additionally, the face of such a second stopper body 21 that is directed to the distal end side is formed as the second stopper distal end face 20a, and the face thereof that is directed to the rear end side is formed as the second stopper rear end face 20b.

The projection portions 22 and 22 are provided in the places that oppose each other at 180° in the circumferential direction of the second stopper body 21, and are provided in the places that are displaced at 90° in the circumferential direction from the T-shaped flat faces 21a and 21a. The faces of the projection portions 22 and 22 that are directed to the radial outside of the axis O are formed in the shape of circular-arc faces with almost the same external diameter as the internal diameter of the inner peripheral surface of the portion 5a to be inserted. As the projection portions 22 and 22 come into close contact with each other, the second stopper 20 is fixed into the portion 5a to be inserted.

The distal end member 25 is an insulating member made of resin, rubber, or the like. Specifically, as shown in FIG. 7, the distal end member is fixed by means, such as a press fitting, from the front end (front end of the second sheath 5) of the portion 5a to be inserted. The distal end member 25 has a distal end lid portion 25a that is located on the distal end side of the second sheath 5, and a cylindrical portion 25b that extends toward the rear end side from distal end lid portion 25a and is fixed to the inner peripheral surface of the portion 5a to be inserted of the second sheath 5. The distal end lid portion 25a is formed with a through hole 25c that penetrates along the axis O and allows the needle-like scalpel 10 to be inserted therethrough. Moreover, the rear end of the cylindrical portion 25b in the distal end member 25 is pinched between the inner peripheral surface of the portion 5a to be inserted of the second sheath 5, and the outer peripheral surface of the second stopper body 21.

In addition, in the present embodiment, when the third stopper 15 and the second stopper 20 abut each other, the distal end lid portion 25a in the distal end member 25 abuts the first stopper 17 simultaneously.

Figure 9:
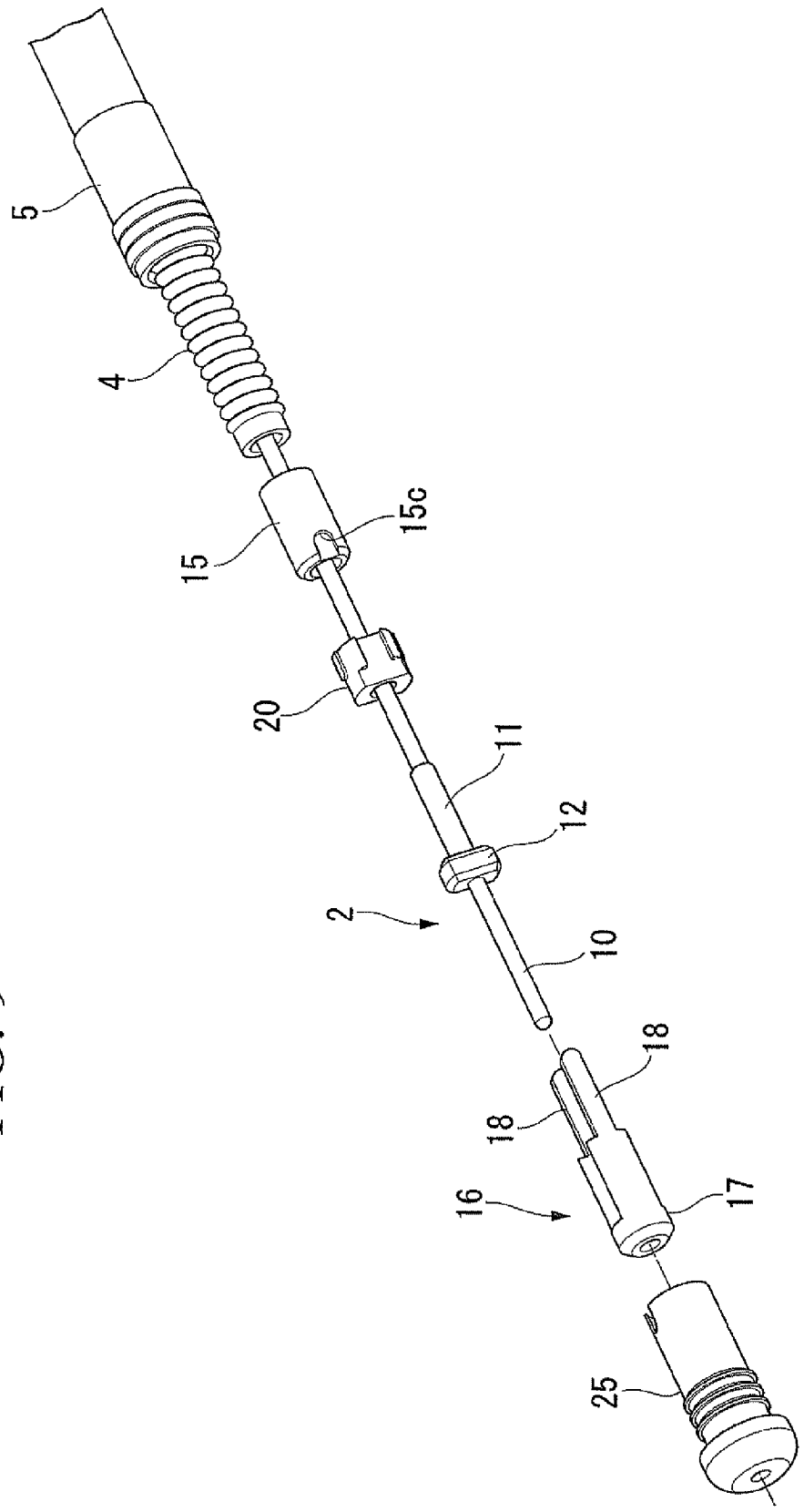
FIG. 9 is a perspective exploded view of the distal end side of the treatment device for an endoscope related to the embodiment.

When the above respective parts are assembled, the first sheath 4 is inserted through the second sheath 5, and the operating wire 3 is inserted through the first sheath 4. Then, as shown in FIG. 9, the distal end of the operating wire 3 is inserted through the third stopper 15 and the second stopper 20 in this order in a state where the distal end of the operating wire 3 is projected from the distal end of the first sheath 4. In this case, the sheath coupling portion 15a of the third stopper 15 is fitted to the distal end of the first sheath 4 from the outside, thereby fixing and integrating the third stopper 15 and the first sheath 4.

Subsequently, the wire coupling portion 11 of the treatment section 2 is coupled to the distal end of the operating wire 3 that is inserted through the third stopper 15 and the second stopper 20. Thereafter, the distal end of the needle-like scalpel 10 of the treatment section 2 is inserted through the first stopper 17 of the guide stopper 16, and the pair of connecting portions 18 and 18 in this guide stopper 16 is coupled to the connecting portion coupling grooves 15c and 15c in the third stopper 15, thereby fixing and integrating the guide stopper 16 and the third stopper 15. In this case, the connecting portion opposed faces 18a of the pair of connecting portions 18 and 18 face or come into slidable contact with the pair of lateral faces 12d and 12d of the locking portion 12 and the pair of T-shaped flat faces 21a and 21a of the second stopper 20 in the treatment section 2. In this way, the second stopper 20 and the locking portion 12 are arranged between the third stopper 15 and the guide stopper 16 so as to be movable in the direction of the axis O.

Next, the third stopper 15, the second stopper 20, the treatment section 2, and the guide stopper 16 are pushed into and inserted into the portion 5a to be inserted of the second sheath 5. In this case, the second stopper 20 abuts and stops at the stepped portion between the portion 5a to be inserted and the other portions in the second sheath 5, and the projection portion 22 of the second stopper 20 comes into close contact with the inner wall of the portion 5a to be inserted. Thereby, the second stopper 20 is brought into the state of being fixed to and integrated with the first sheath 4. Then, the distal end of the needle-like scalpel 10 that is inserted through the first stopper 17 is inserted through the through hole 25c of the distal end lid portion 25a in the distal end member 25, and thereafter, the cylindrical portion 25b of the distal end member 25 is inserted into the portion 5a to be inserted of the second sheath 5.

By performing assembling as described above, as shown in FIGS. 2 to 4, the first stopper 17 is fixed to the first sheath 4 via the connecting portions 18 and 18 that extend toward the front side from the distal end of the first sheath 4, and the second stopper 20 is fixed to the second sheath 5 on the rear side of the first stopper 17. Additionally, the third stopper 15 capable of abutting the first stopper 17 is fixed to the distal end of the first sheath 4, and the connecting portions 18 and 18 are provided with the fourth stopper 19 capable of abutting the first stopper 17. Moreover, the distal end member 25 capable of abutting the first stopper 17 is brought into the state of being fixed to the distal end of the second sheath.

Next, the configuration of the operating section 6 will be described with reference to FIG. 1 and FIGS. 10, 11A, and 11B.

The operating section 6 includes an elongated operating section body 30 that extends along the axis O, and the wire operating portion 7 and the sheath operating portion 8 constitutes the operating section body 30.

The operating section body 30, as shown in FIG. 1, includes a finger hook handle 31a for hooking a finger, on the proximal end (rear end) side thereof at the time of operation. A slit portion 31 that passes through the operating section body 30 in the diametrical direction of the axis O is formed at a portion closer to the proximal end side than the center of the operating section body 30 in the direction of the axis O. The portion closer to the front side (distal end side) than the center of the operating section body 30 in the direction of the axis O is formed with a cut-out groove portion 32 obtained by cutting out the operating section body 30 in the radial direction of the axis O.

The operating section body 30 is formed with a wire insertion hole 34 that is bored along the axis O so as to allow the slit portion 31 and the cut-out groove portion 32 to communicate with each other and that allows the operating wire 3 to be inserted therethrough. The wire insertion hole 34 has a diameter that is equal to or slightly greater than that of the operating wire 3, and thereby, the operating wire 3 is slidably inserted through the wire insertion hole 34.

Moreover, the operating section body 30 is formed with a sheath insertion hole 35 that is bored along the axis O so as to allow the distal end of the operating section body 30 and the cut-out groove portion 32 to communicate with each other and that allows the second sheath 5 through which the first sheath 4 and the operating wire 3 are inserted to be inserted therethrough. The sheath insertion hole 35 has a diameter that is equal to that of the second sheath 5 or is slightly greater than the second sheath 5, and thereby, the second sheath 5 is allowed to move relative to the operating section body 30 in the direction of the axis O in the state of being inserted through the sheath insertion hole 35.

As shown in FIG. 1, the wire operating portion 7 is provided in the vicinity of the slit portion 31 of the operating section body 30, and includes a slider 40 and a plug 43.

The slider 40 has a substantially cylindrical shape that is slidably and externally fitted to the outer peripheral side of the operating section body 30 within a predetermined range in the direction of the axis O. A pair of distal end finger hook portions 41 and 41 that extends toward both sides, respectively, in the diametrical direction of the axis O is formed on the distal end side of the slider 40. Additionally, a pair of rear end finger hook portions 42 and 42 that extends toward both sides, respectively, in the diametrical direction of the axis O is formed on the rear end side of the slider 40.

One distal end finger hook portion 41 of the distal end finger hook portions 41 and 41 in the slider 40 is formed with a plug housing hole 40c that penetrates from the radial outside of the axis O toward the inside thereof. The plug 43 is housed within the plug housing hole 40c.

A power cable connected to a high-frequency power source (not shown) is connected to the plug 43, and is arranged so as to be exposed to the slit portion 31 of the operating section body 30 over the pair distal end finger hook portions 41 and 41 in the state of being housed within the plug housing hole 40c. A rear end of the operating wire is connected to the portion of the plug 43 exposed to the slit portion 31.

By adopting such a configuration, the plug 43 is made movable in the direction of the axis O inside the slit portion 31. When a finger is hooked between the distal end finger hook portions 41 and 41 and the rear end finger hook portion 42 and 42 of the slider 40 and the slider 40 is made to slide in the direction of the axis O, the operation is transmitted to the operating wire 3 via the plug 43, and the operating wire 3 moves along the direction of the axis O.

In addition, as shown in FIG. 1, the rear end of the first sheath 4 is fixed to the wall surface of the cut-out groove portion 32 of the operating section body 30 to which the wire insertion hole 34 opens, via a fixing member 5b. Accordingly, when the operating wire 3 is moved by operating the slider 40 of the wire operating portion 7, only the operating wire 3 moves, and the first sheath 4 is brought into a stopped state. That is, by operating the wire operating portion 7, the operating wire 3 moves relative to the first sheath 4 in the direction of the axis O.

Moreover, a high-frequency power source can be electrically connected to the operating wire 3 via the plug 43 by inserting a power cable into the plug housing hole 40c to couple the power cable to the plug 43.

Figure 10:
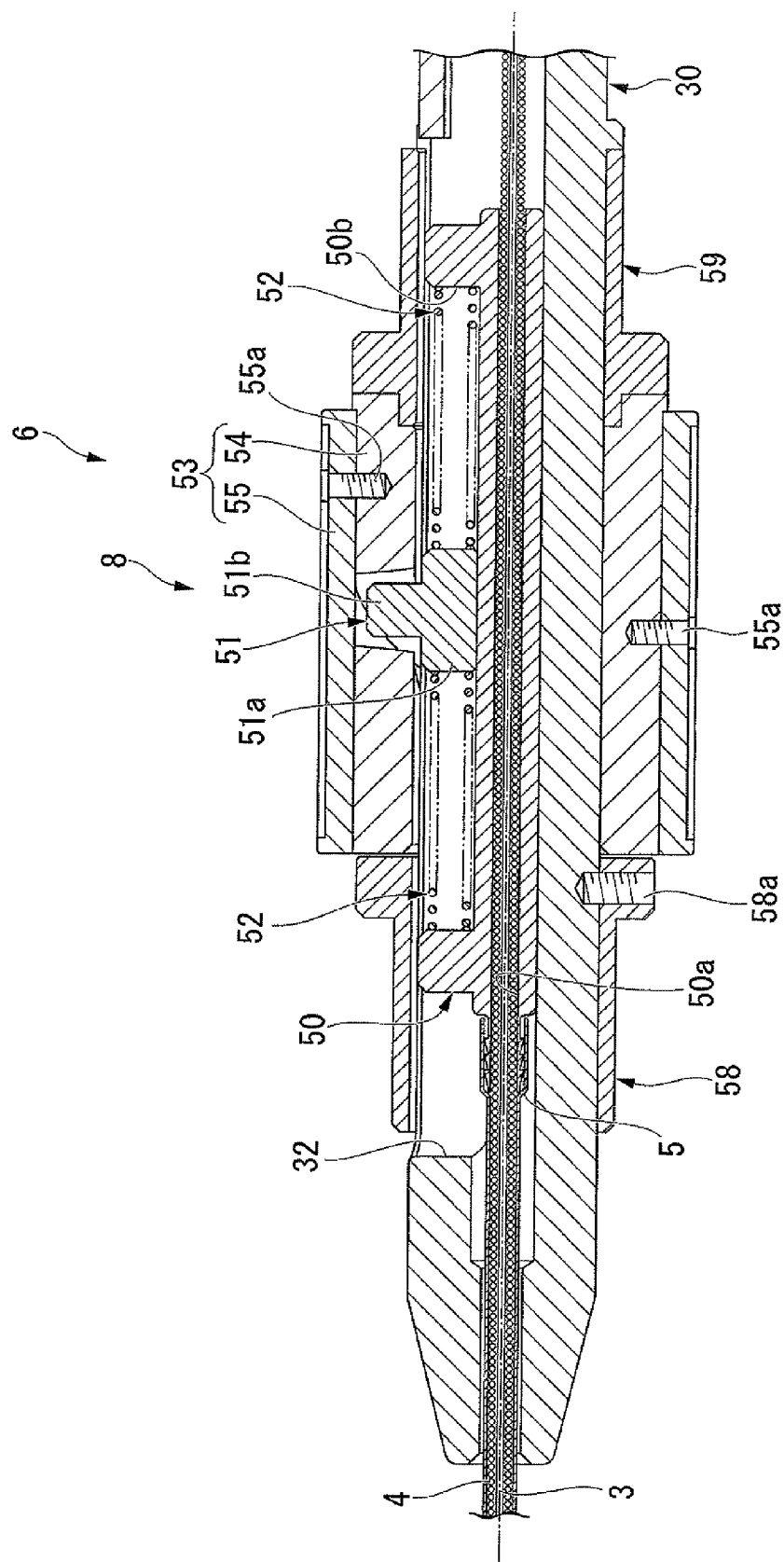
FIG. 10 is a longitudinal cross-sectional view showing a sheath operating portion in an operating section.

Specifically, as shown in FIG. 10, the sheath operating portion 8 includes a second sheath fixing member 50, a movable member 51, an elastic member 52, a rotation handle section 53, and a front side supporting member 58 and a rear side supporting member 59.

The second sheath fixing member 50 is a member that has a substantially cylindrical shape, and has a first sheath insertion hole 50a that is bored along the axis O and that allows the first sheath 4 to be inserted therethrough. The internal diameter of the first sheath insertion hole 50a is set to be almost equal to or slightly greater than the external diameter of the first sheath 4, and the first sheath 4 and the second sheath fixing member 50 are made slidable on each other. Accordingly, the second sheath fixing member 50 and the first sheath 4 can move relative to each other without interference with mutual operations in the direction of the axis O.

A rear end of the second sheath 5 is coupled to a distal end of the second sheath fixing member 50. Thereby, the second sheath fixing member 50 and the second sheath 5 are fixed to and integrated with each other.

Moreover, the outer peripheral surface of the second sheath fixing member 50 is formed with a movable member housing groove 50b that is cut out along the direction of the axis O and has a substantially U-shaped shape in a cross-section including the axis O.

The movable member 51 is a member that has a substantially T-shaped shape in a cross-sectional view including the axis O, and includes a movable member body 51a and a protruding portion 51b.

The movable member body 51a is arranged so as to be movable in the direction of the axis O within the movable member housing groove 50b. The thickness of the movable member body 51a in the radial direction of the axis O is made almost equal to the depth of the movable member housing groove 50b. Thereby, the whole movable member body 51a is brought into a state of being housed within the movable member housing groove 50b. In this state, the movable member body slidably abuts the bottom face of the movable member housing groove 50b, and is made movable in the direction of the axis O within the movable member housing groove 50b. In addition, the movable member body 51a comes into contact with the movable member housing groove 50b on both sides in the circumferential direction of the axis O, and the movable member body 51a does not move in the circumferential direction. That is, the movable member 51 is made movable only in the direction of the axis O.

The protruding portion 51b is formed so as to protrude in a columnar shape to the radial outside of the axis O from the movable member main body 51a, and thereby, the protruding portion 51b is configured so as to protrude to the radial outside of the axis O from the movable member housing groove 50b.

As such, a pair of coil-spring-shaped elastic members 52 and 52 that extends parallel to the axis O is arranged on the front side and rear side, in the direction of the axis O, of the movable member body 51a housed within the movable member housing groove 50b. Each elastic member 52 and 52 has one end connected to a wall surface on the front side or rear side of the movable member housing groove 50b and the other end connected to the elastic member 52 or 52. Thereby, the movable member 51 is brought into the state of being connected to the second sheath fixing member 50 via the pair of elastic members 52 and 52 arranged on both sides in the direction of the axis O. The movable member 51 is biased to the central position of the movable member housing groove 50b in the direction of the axis O by the elastic members 52 and 52.

The rotation handle section 53 includes a rotation handle section body 54 that is rotatably fitted to the outer peripheral side of the operating section body 30, and a manual turning portion 55 that is fitted to the outer peripheral side of the rotation handle section body 54.

The rotation handle section body 54 has a substantially cylindrical shape having the axis O as a center, and the internal diameter thereof is set to be almost equal to or slightly greater than the operating section body 30. As the a rotation handle section body 54 is fitted to the operating section body 30, the rotation handle section body 54 and the operating section body 30 are made movable relative to each other in the circumferential direction.

Figure 11A:
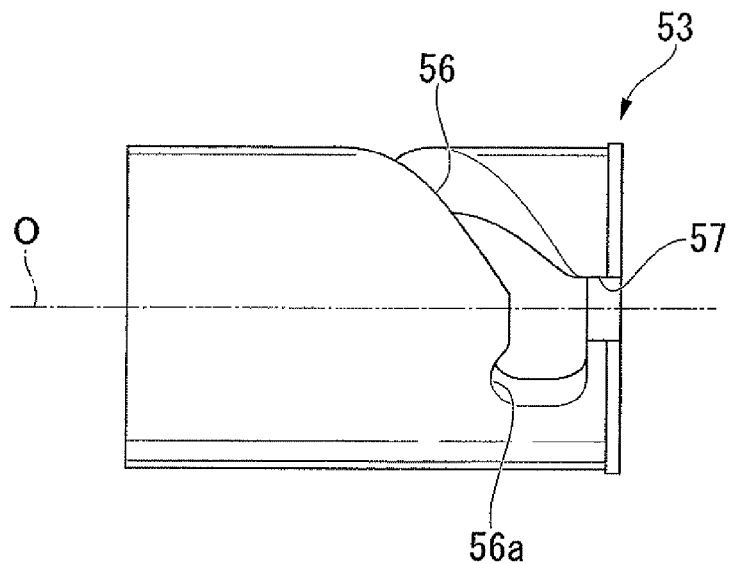
FIG. 11A is a side view of a rotation handle section body.
Figure 11B:
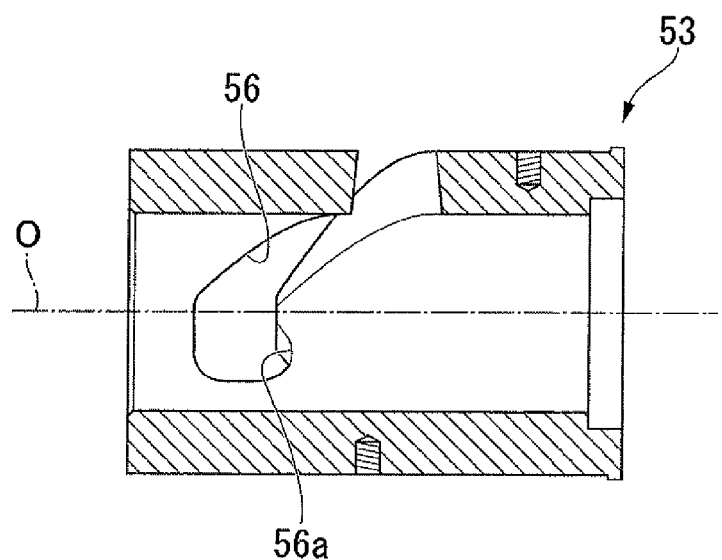
FIG. 11B is a longitudinal cross-sectional view of the rotation handle section body.

Specifically, as shown in FIGS. 11A and 11B, the rotation handle section body 54 is formed with a cam groove 56 that is twisted in the clockwise direction with the axis O as a center as it goes to the front side in the direction of the axis O. The cam groove 56 is a groove into which the protruding portion 51b of the movable member 51 is inserted when the rotation handle section body 54 is fitted to the operating section body 30. An introducing groove 57 for introducing the protruding portion 51b into the cam groove 56 from a rear end is formed on the rear end side of the rotation handle section body 54. The protruding portion 51b introduced into the cam groove 56 from the introducing groove 57 moves within a range of the formation of the cam groove 56 with the rotational operation of the rotation handle section body 54 around the axis O, and the movable member 51 moves in the direction of the axis O in connection with this movement.

Protruding portion fixing grooves 56a, which are formed so as to be recessed toward an inward direction in the direction of the axis O as seen from both ends of the cam groove 56, are formed at both ends of the cam groove 56.

A cylindrical manual turning portion 55 that has the same internal diameter as the external diameter of the rotation handle section body 54 is fitted to the outer peripheral side of such a rotation handle section body 54, and the manual turning portion 55 and the rotation handle section body 54 are fixed by screws 55a. Thereby, when the manual turning portion 55 is rotated around the axis O, the rotation handle section body 54 rotates around the axis O similarly.

In addition, it is preferable that the outer peripheral surface of the manual turning portion 55 be formed with irregularities for preventing slipping when the manual turning portion 55 is rotated.

The front side supporting member 58 is a cylindrical member that is fitted to the operating section body 30 on the front side of the rotation handle section 53 in the direction of the axis O, and is fixed to and integrated with the operating section body 30 via screws 58a. The rear side supporting member 59 is a cylindrical member that is fitted to the operating section body 30 on the rear side of the rotation handle section 53 in the direction of the axis O, and is fixed to and integrated with the operating section body 30 via screws (not shown).

The distance between a rear end of the front side supporting member 58 and a front end of the rear side supporting member 59 is set to be almost equal to the dimension of the rotation handle section 53 in the direction of the axis O. That is, the rotation handle section 53 is supported and fixed so as to be pinched by the front side supporting member 58 and the rear side supporting member 59 from both sides in the direction of the axis O.

In such a sheath operating portion 8, the position of the second sheath 5 in the direction of the axis O can be displaced by operating the rotation handle section 53.

That is, when the manual turning portion 55 of the rotation handle section 53 is rotated around the axis O, the rotation handle section body 54 also rotates around the axis O in connection with this rotation. Then, as the protruding portion 51b within the cam groove 56 of the rotation handle section body 54 moves along the cam groove 56, the movable member 51 moves within the movable member housing groove 50b to the front side or rear side in the direction of the axis O along the axis O. The movement of the movable member 51 is transmitted to the second sheath fixing member 50 via the elastic members 52 and 52. Thereby, the second sheath 5 connected to the second sheath fixing member 50 is displaced in the direction of the axis O.

Additionally, when the rotation handle section 53 is stopped to turn in one direction or the other direction around the axis O, the protruding portion 51b of the movable member 51 fits into the protruding portion fixing grooves 56a and 56a formed at both ends of the cam groove 56. In this case, as the movable member 51 is biased toward the center in the direction of the axis O by the pair of elastic members 52 and 52, the protruding portion 51b does not escape from the protruding portion fixing grooves 56a and 56a simply by rotating the rotation handle section 53 with a slight force. Thereby, the position of the movable member 51 can be fixed. In addition, in this case, if the rotation handle section 53 is rotated only by a force that resists the biasing forces of the elastic members 52 and 52, fixation of the movable member 51 can be easily released.

Next, the action of the treatment device 1 of the above configuration will be described. In the treatment device 1 of the present embodiment, as shown in FIGS. 12A to 12D and 13A to 13D, the length of the protruding length L of the needle-like scalpel 10 in the treatment section 2, that is, the protruding length L of the needle-like scalpel 10 from the distal end member 25 can be adjusted in three steps. Such adjustment is performed by the operation of the first sheath 4 by the sheath operating portion 8 in the operating section 6 and the operation of the operating wire 3 by the wire operating portion 7.

Here, since the first sheath 4 is not a target to be operated by the operating section 6, the position of the first sheath 4 in FIGS. 12A to 12D and 13A to 13D is fixed in the direction of the axis O. Accordingly, the positions of the third stopper 15 and the guide stopper 16 that are fixed to and integrated with the first sheath 4 are also fixed in the direction of the axis O. Hence, when the wire operating portion 7 and the sheath operating portion 8 are operated, the operating wire 3 and the second sheath 5 move relatively in the direction of the axis O on the basis of the positions of the first sheath 4, the third stopper 15, and the guide stopper 16 in the direction of the axis O. Then, as the operating wire 3 and the second sheath 5 move relatively in this way, the distal end portion of the treatment device 1 shows the four forms of FIGS. 12A to 12D and 13A to 13D that will be described below in detail.

First, the operation of the second sheath 5 by the sheath operating portion 8 will be described.

As the rotation handle section 53 of the sheath operating portion 8 is rotated in one direction, the second sheath 5 is retreated to the rear side in the direction of axis O. Then, as shown in FIGS. 12A and 12B or FIGS. 13A and 13B, the second stopper 20 that is fixed to and integrated with the second sheath 5 also retreats. In this case, retreat movement of the second sheath 5 is regulated as the second stopper 20 abuts the third stopper 15. As such, the positional relationship in which the second sheath 5 retreats and the second stopper 20 and the third stopper 15 abut each other is defined as a first positional relationship.

In the state of this first positional relationship, the second stopper 20 that is fixed to and integrated with the second sheath 5 is brought into a retreat state. Hence, the first stopper 17 and the second stopper 20 are brought into a state of maximum separation, and the distance D between the first stopper 17 and the second stopper 20 is defined as the largest D1 (refer to FIGS. 12A and 12B).

Figure 13A:
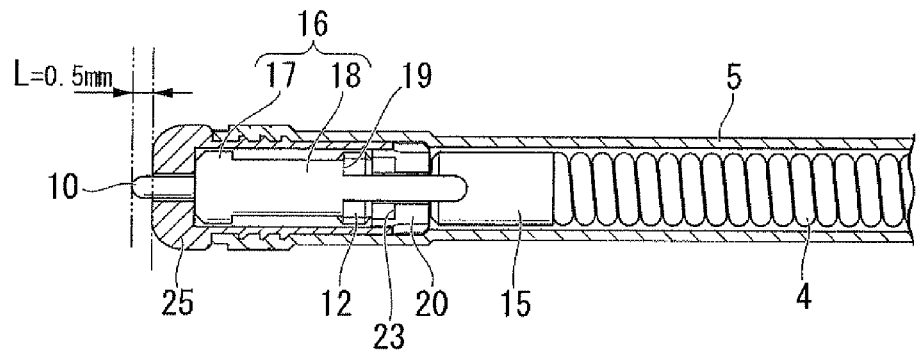
FIG. 13A is a side view showing each form on the distal end side of the treatment device for an endoscope related to the embodiment.
Figure 13B:
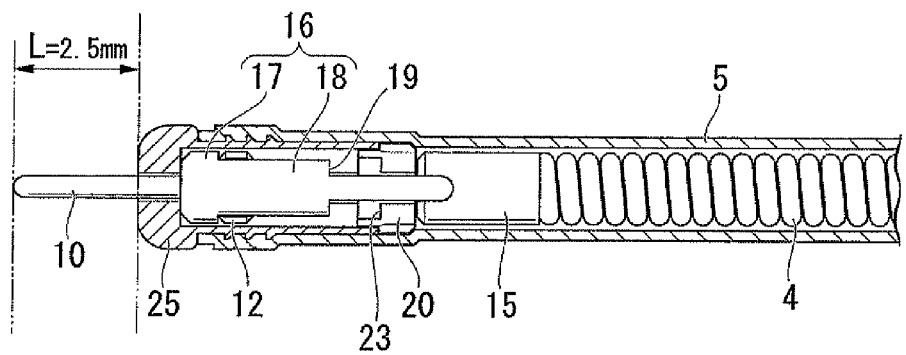
FIG. 13B is a side view showing each form on the distal end side of the treatment device for an endoscope related to the embodiment.
Figure 13C:
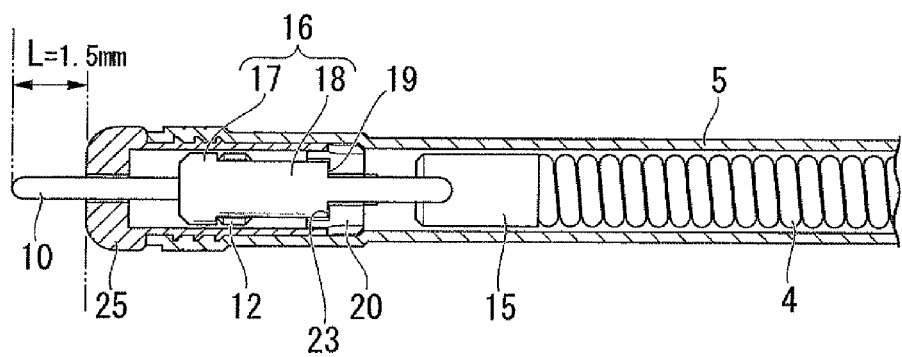
FIG. 13C is a side view showing each form on the distal end side of the treatment device for an endoscope related to the embodiment.
Figure 13D:
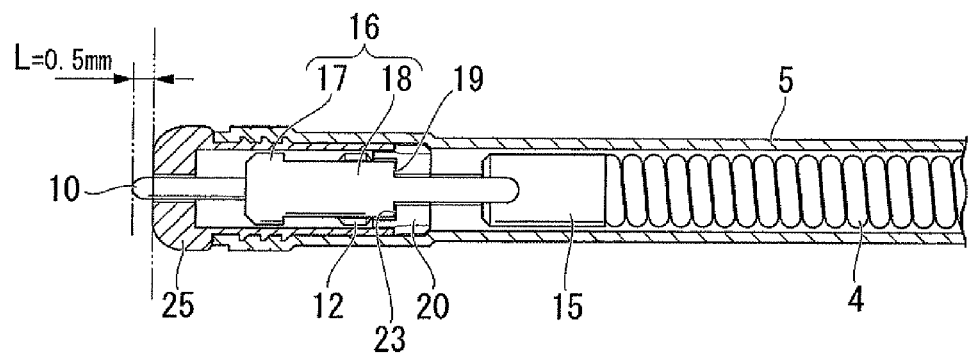
FIG. 13D is a side view showing each form on the distal end side of the treatment device for an endoscope related to the embodiment.

Additionally, the rotation handle section 53 is rotated in the other direction opposite to the one direction to advance the second sheath 5 to the front side of the axis O. Then, as shown in FIGS. 12C and 12D or FIGS. 13C and 13D, the second stopper 20 that is fixed to and integrated with the second sheath 5 also advances. In this case, as shown in FIGS. 13C and 13D, the advance movement is regulated as the fourth stopper abutting face 23 of the second stopper 20 abuts the fourth stopper 19 of the connecting portion 18. That is, the first sheath 4 advances to a position where the fourth stopper abutting face 23 of the second stopper 20 abuts the fourth stopper 19. As such, the positional relationship in which the second sheath 5 advances and the second stopper 20 and the fourth stopper 19 abut each other is defined as a second positional relationship.

In the state of this second positional relationship, the second stopper 20 that is fixed to and integrated with the second sheath 5 is brought into an advanced state. Hence, the first stopper 17 and the second stopper 20 are brought into a maximum approached state, and the distance D between the first stopper 17 and the second stopper 20 is defined as the smallest D2 (refer to FIGS. 12C and 12D).

In this way, the second sheath 5 is allowed to advance or retreat in the direction of the axis O between the first positional relationship regulated by the third stopper 15 and the second positional relationship regulated by the fourth stopper 19. Since the distal end member 25 fixed to the second sheath 5 is displaced by the advance or retreat movement of this second sheath 5, the protruding length L of the treatment section 2 can be changed by the advance or retreat movement of the second sheath 5. In addition, in the present embodiment, the displacement width of the second sheath 5 in the direction of the axis O in the first positional relationship and the second positional relationship is set to 1.0 mm. Accordingly, the protruding length L of the treatment section 2 can be changed by 1.0 mm according to the displacement width of the second sheath 5 by operating the sheath operating portion 8. Additionally, along with this, a difference between the distances D1 and D2 both defined by a distance between the first stopper 17 and the second stopper 20 also become 1.0 mm.

In addition, the movement width of the movable member 51 in the direction of the axis O caused by the operation of the rotation handle section 53 is set to a value that is greater than 1.0 mm that is the displacement width in the first positional relationship and the second positional relationship of the second sheath 5. Thereby, when the rotation handle section 53 is operated, the second sheath 5 can be reliably displaced in the first positional relationship and the second positional relationship. In addition, since a distance equivalent to the travel distance of the movable member 51 beyond the displacement width of the second sheath 5 is filled as the elastic member 52 is compressed or expanded, the operation of the rotation handle section 53 is not obstructed.

Next, the operation of the operating wire 3 caused by the wire operating portion 7 will be described.

When the slider 40 of the wire operating portion 7 is moved to the rear side in the direction of axis O, as shown in FIGS. 12A, 12B, 13A, and 13B, the operating wire 3 retreats to a position where the locking portion 12 of the treatment section 2 coupled to the operating wire 3 abuts the second stopper 20. As such, a state where the locking portion 12 retreats and abuts the second stopper 20 is defined as a retreat state of the operating wire 3.

Additionally, when the slider 40 of the wire operating portion 7 is moved to the front side in the direction of the axis O, as shown in FIGS. 12B, 12C, 13B, and 13C, the operating wire 3 advances to a position where the locking portion 12 of the treatment section 2 coupled to the operating wire 3 abuts the first stopper 17. As such, a state where the locking portion 12 advances and abuts the first stopper 17 is defined as an advanced state of the operating wire 3.

That is, the advance or retreat movement of the operating wire 3 in the direction of the axis O is regulated by the first stopper 17 and the second stopper 20, and the movable region of the operating wire 3 varies according to the distance D between the first stopper 17 and the second stopper 20 in the direction of the axis O.

That is, in a case where the second sheath 5 is in the first positional relationship, the operating wire 3 performs advance or retreat movement with the distance D1 as a movable region. In the present embodiment, the operating wire is allowed to advance or retreat by 2.0 mm in the direction of the axis O. On the other hand, in a case where the second sheath 5 is in the second positional relationship, the operating wire 3 performs advance or retreat movement with the distance D2 as a movable region. In the present embodiment, the operating wire is allowed to advance or retreat by 1.0 mm.

Figure 12A:
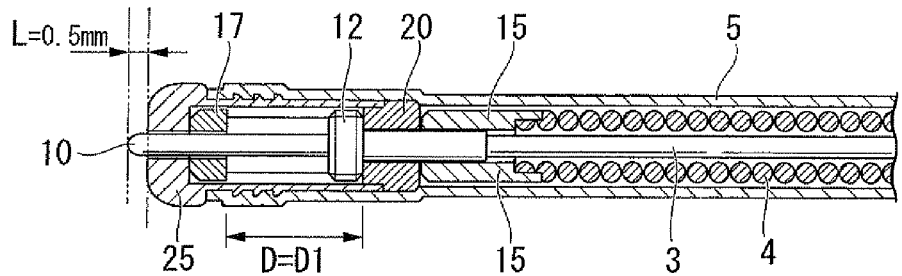
FIG. 12A is a longitudinal cross-sectional view showing each form on the distal end side of the treatment device for an endoscope related to the embodiment.
Figure 12B:
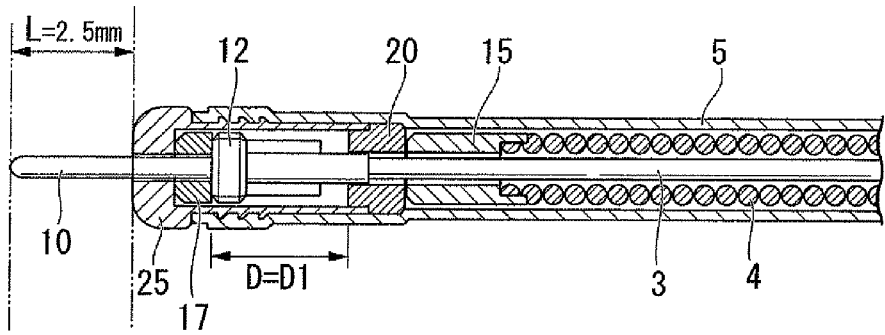
FIG. 12B is a longitudinal cross-sectional view showing each form on the distal end side of the treatment device for an endoscope related to the embodiment.
Figure 12C:
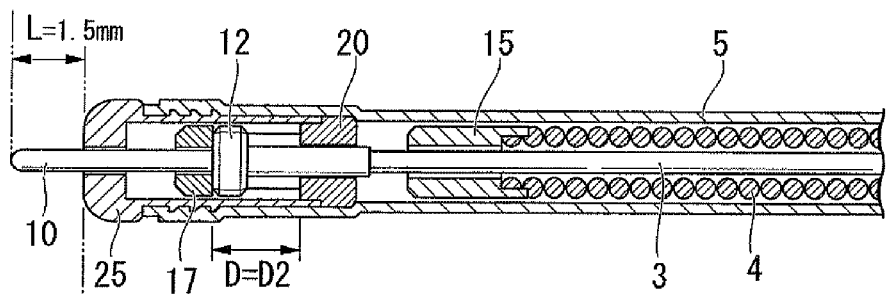
FIG. 12C is a longitudinal cross-sectional view showing each form on the distal end side of the treatment device for an endoscope related to the embodiment.
Figure 12D:
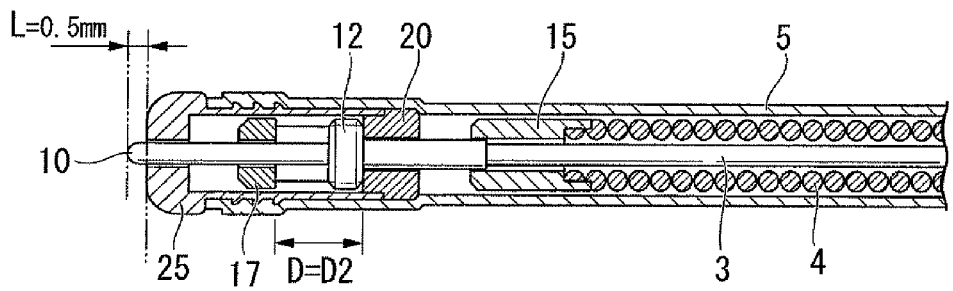
FIG. 12D is a longitudinal cross-sectional view showing each form on the distal end side of the treatment device for an endoscope related to the embodiment.

Next, respective forms of the distal end of the treatment device 1 of FIGS. 12A to 12D and 13A to 13D will be described. FIG. 12A and FIG. 13A show a first form of the distal end of the treatment device 1. In this first form, the second sheath 5 is located in the first positional relationship, and the operating wire 3 is brought into the retreat state. Thereby, the protruding length of the needle-like scalpel 10 is set to as L=0.5 mm as the smallest protruding length.

When the operating wire 3 is brought into the advanced state by the operation of the wire operating portion 7 in the state of the first form, the distal end of the treatment section 2 shifts to a second form. That is, as shown in FIGS. 12B and 13B, in the second form, the second sheath 5 is located in the first positional relationship. Therefore, the distance between the first stopper 17 and the second stopper 20 is set to D=D1, and the operating wire 3 is allowed to be displaced by 2.0 mm in the direction of the axis O. Thereby, when the operating wire 3 is advanced, the needle-like scalpel 10 advances by 2.0 mm. Accordingly, the protruding length L of the needle-like scalpel 10 in the second form is given by adding 2.0 mm to 0.5 mm in the first form, and the protruding length L=2.5 mm.

As such, in a state where the second sheath 5 is in the first positional relationship by the operation of the sheath operating portion 8, the protruding length L of the treatment section 2 can be adjusted to 0.5 mm and 2.5 mm, that is, can be adjusted with a width of 2.0 mm, by the operation of the wire operating portion 7.

That is, in a case where the second sheath 5 is in the first positional relationship, marking can be performed on an affected part in a state where the protruding length L of the treatment section 2 is set to 0.5 mm, and a comparatively large incision can be performed on the affected part by projecting the treatment section 2 so that the protruding length L of becomes by 2.0 mm.

Subsequently, in the state of the second form, when the second sheath 5 is advanced by the operation of the sheath operating portion 8 and is displaced to the second positional relationship, the distal end of the treatment device 1 shifts to a third form. That is, when the second sheath 5 is moved to the second positional relationship from the first positional relationship, as described above, the second sheath 5 moves forward by 1.0 mm, and the distal end member 25 provided at the front end of the second sheath 5 moves forward along with this. Then, since the distal end of the distal end member 25 that becomes the basis of the protruding length L of the needle-like scalpel 10 also advances by 1.0 mm, the protruding length L becomes small by 1.0 mm. Accordingly, the protruding length L of the needle-like scalpel 10 in the third form becomes smaller by 1.0 mm from 2.5 mm in the second form, and the protruding length L=1.5 mm.

Next, in the state of the third form, when the operating wire 3 is moved from the advanced state to the retreat state by operating the wire operating portion 7, shift to the fourth form is made. In this case, as described above, since the second sheath 5 is located in the second positional relationship, the distance between the first stopper 17 and the second stopper 20 is set to D=D2, and the operating wire 3 is allowed to be displaced by 1.0 mm in the direction of the axis O. Thereby, when the operating wire 3 is retreated, the needle-like scalpel 10 retreats by 1.0 mm. Accordingly, the protruding length L of the needle-like scalpel 10 in the fourth form becomes smaller by 1.0 mm from 1.5 mm in the third form, and the protruding length L=0.5 mm.

As such, in a state where the second sheath 5 is in the second positional relationship by the operation of the sheath operating portion 8, the protruding length L of the treatment section 2 can be adjusted to 0.5 mm and 1.5 mm, that is, can be adjusted with a width of 1.0 mm, by the operation of the wire operating portion 7.

That is, in a case where the second sheath 5 is in the second positional relationship, marking can be performed on an affected part in a state where the protruding length L of the treatment section 2 is set to 0.5 mm, and a comparatively small incision can be performed on the affected part by projecting the treatment section 2 so that the protruding length L of becomes by 1.5 mm.

As described above, according to the treatment device 1 of the present embodiment, the first stopper 17 and the second stopper 20 that regulate the movement of the locking portion 12 integrally provided in the operating wire 3 are provided. Thus, when the wire operating portion 7 is operated, the operating wire 3 can be displaced in two steps in the direction of the axis O according to the distance D between the first stopper 17 and the second stopper 20. Additionally, the second sheath 5 can be displaced in two steps in the first positional relationship and the second positional relationship by the operation of the sheath operating portion 8.

Accordingly, the protruding length L of the treatment section 2 from the distal end (distal end member 25) of the second sheath 5 can be easily and reliably adjusted and maintained in multiple steps by performing the operation of the operating wire 3 and the second sheath 5 in combination.

Additionally, in the present embodiment, in a case where the second sheath 5 is in the first positional relationship and the second positional relationship, the distance D between the first stopper 17 and the second stopper 20 in the direction of the axis O varies. Thereby, the adjustment width of the protruding length L of the operating wire 3 caused by the operation of the wire operating portion 7 can be changed according to the first positional relationship and the second positional relationship. Accordingly, for example, in a treatment that needs to increase the adjustment width of the protruding length L, the second sheath 5 is brought into the state of the first positional relationship, and in a treatment that needs to decrease the adjustment width of the protruding length L, the second sheath 5 is brought into the state of the second positional relationship. It is thereby possible to respond flexibly to various treatments.

Additionally, in the present embodiment, the distal end of the first sheath 4 is provided with the third stopper 15 that abuts the second stopper 20 in the first positional relationship to restrict retreat movement of the second sheath 5. For this reason, when the second sheath 5 is retreated by the operation of the sheath operating portion 8, the second sheath 5 can be easily positioned at the position of the first positional relationship, and the state of the first positional relationship can be held.

Additionally, in a case where the second sheath 5 is in the first positional relationship in this way, the distal end member 25 abuts the first stopper 17 to regulate retreat movement of the second sheath 5. Thus, positioning and maintenance of the first positional relationship can be more reliably performed.

Moreover, the connecting portions 18 and 18 are formed with the fourth stopper 19 that abuts the second stopper 20 in the second positional relationship to regulate advance movement of the second sheath 5. For this reason, when the second sheath 5 is advanced by the operation of the sheath operating portion 8, the second sheath 5 can be easily positioned at the position of the second positional relationship, and the state of the second positional relationship can be held.

In this way, according to the treatment device 1 of the present embodiment, the protruding length L of the treatment section 2 can be reliably and easily adjusted in multiple steps without performing minute adjustment according to manipulation by a worker.

Moreover, since the sheath operating portion 8 can be operated by rotating the rotation handle section 53 around the axis O, the second sheath 5 can be more easily and simply moved.

Additionally, the operation caused by the above sheath operating portion 8 can be realized by adopting a configuration in which the cam groove 56 is formed in the rotation handle section body 54 in the rotation handle section 53, and the protruding portion 51b of the movable member 51 connected to the second sheath 5 is inserted into the cam groove 56.

Here, the second sheath 5 has a long tube shape, and when a treatment is performed using the treatment device 1, the second sheath 5 is brought into a bent state or a looped state. In this case, even if the movable member 51 being moved by a predetermined distance in the direction of the axis O, the second sheath 5 may be influenced by bending or looping, and the second sheath 5 may not be able to move in the direction of the axis O by a desired distance. In this case, a gap may occur in the travel distance between the movable member 51 and the second sheath 5, and this may cause the loosening of the second sheath 5 or the failure of treatment device 1 itself.

In this respect, in the treatment device 1 related to the present embodiment, even if the bent or looped second sheath 5 has not moved by a desired distance when the movable member 51 is moved, a gap in travel distance between the movable member 51 and the second sheath 5 can be filled as the elastic members 52 and 52 are compressed or expanded. Accordingly, there is no case in which loosening occurs in the second sheath 5 or failure occurs as described above. Additionally, if the bending or looping of the second sheath 5 is returned, the second sheath 5 is moved by biasing forces of the compressed or expanded elastic members 52 and 52. This can eliminate the influence caused by the bending or looping of the second sheath 5. Therefore, it is possible to provide a user-friendly treatment device 1.

Although the treatment device 1 that is the embodiment of the present invention has been described hitherto, the present invention is not limited thereto, and can be appropriately changed without departing from the technical idea thereof.

For example, in the embodiment, the second sheath 5 is positioned and held in the first positional relationship as the third stopper 15 abuts the second stopper 20 and the distal end member 25 abuts the first stopper 17. However, the present invention is not limited thereto. A configuration in which at least any one of abutment of the third stopper 15 onto the second stopper 20 and abutment of the distal end member 25 onto the first stopper 17 is performed may be adopted. Even by this, the second sheath 5 can be reliably positioned and held in the first positional relationship.

Additionally, although the configuration in which the treatment section 2 is provided with the locking portion 12 is adopted in the embodiment, a configuration in which the operating wire 3 is provided with the locking portion 12 may be adopted. Even by this, as the locking portion 12 abuts the first stopper 17 and the second stopper 20, the protruding length L of the treatment section 2 integrally provided in the operating wire 3 can be adjusted in two steps when the wire operating portion 7 is operated.

The distances D1 and D2 between the first stopper 17 and the second stopper 20 can be arbitrarily set according to the design of arrangement places of the first stoppers 17 and the second stopper 20. Thereby, the adjustment width of the protruding length L of the treatment section 2 in a case where the second sheath 5 is in the first positional relationship and the second positional relationship can be freely set.

Moreover, in the embodiment, the protruding length L of the treatment section 2 can be set to 0.5 mm and 2.5 mm in a case where the second sheath 5 is in the first positional relationship. The protruding length L of the treatment section 2 can be set to 0.5 mm to 1.5 mm in a case where the second sheath 5 is in the second positional relationship. Thereby, the protruding length L of the treatment section 2 can be adjusted to a total of three protruding lengths L of 0.5 mm, 1.5 mm, and 2.5 mm. However, it is possible to make the minimums of the protruding length L in the first positional relationship and the second positional relationship of the second sheath 5 different from each other, thereby adjusting the protruding length to a total of four protruding lengths L to the maximum. Even in this case, the protruding length L can be set to four arbitrary values by appropriately designing respective parts.

Although a preferable embodiment of the present invention has been described hitherto, the present invention is not limited to the embodiment. Additions, omissions, substitutions, and other modifications can be made without departing from the scope of the present invention. Accordingly, the present invention is not to be considered as being limited by the foregoing description, and is only limited by the scope of the appended claims.

The invention claimed is:

1. A treatment device for an endoscope comprising:
an operating wire having a treatment section that performs a treatment on a tissue in a body cavity at a distal end thereof and being capable of being advanced or retreated in the direction of an axis;
a first sheath through which the operating wire is inserted;
a second sheath into which the first sheath is inserted and from a distal end of which the treatment section protrudes;
a locking portion provided in the operating wire or the treatment section to advance or retreat in the direction of the axis with advance or retreat operation of the operating wire;
a first stopper being provided in the first sheath via a connecting portion that extends toward the front side from a distal end of the first sheath, the first stopper regulating advance movement of the locking portion;
a second stopper being provided in the second sheath on the rear side of the first stopper in the direction of the axis, the second stopper regulating retreat movement of the locking portion; and
a sheath operating portion that advances or retreats the second sheath between a first positional relationship and a second positional relationship such that the second sheath has different positions relative to the first sheath in the direction of the axis.

2. The treatment device for an endoscope according to claim 1, wherein the distance between the first stopper and the second stopper in the direction of the axis varies in a case where the second sheath is located in the first positional relationship and a case where the second sheath is located in the second positional relationship.

3. The treatment device for an endoscope according to claim 1, further comprising a third stopper provided at a distal end of the first sheath to abut the second stopper in the first positional relationship to restrict retreat movement of the second sheath with respect to the first sheath.

4. The treatment device for an endoscope according to claim 1, further comprising a distal end member provided at a distal end of the second sheath to abut the first stopper in the first positional relationship to restrict retreat movement of the second sheath with respect to the first sheath.

5. The treatment device for an endoscope according to claim 2, further comprising a fourth stopper provided at the connecting portion to abut the second stopper in the second positional relationship to restrict advance movement of the second sheath with respect to the first sheath.

6. The treatment device for an endoscope according to claim 1, wherein the sheath operating portion includes a rotation handle section allowed to be rotationally operated around the direction of the axis, and the second sheath moves in the direction of the axis relative to the first sheath by rotationally operating the rotation handle section.

7. The treatment device for an endoscope according to claim 1, further comprising a cam groove formed in an inner peripheral surface of the rotation handle section that has a cylindrical shape and twisted around the axis, and a movable member made movable in the direction of the axis and connected to the second sheath,
wherein a portion of the movable member is inserted into the cam groove.

8. The treatment device for an endoscope according to claim 7, further comprising a pair of elastic members respectively provided on both sides of the movable member in the direction of the axis to connect the movable member and the second sheath.

* * * * *